US010661060B2

(12) United States Patent
Niazi

(10) Patent No.: US 10,661,060 B2
(45) Date of Patent: May 26, 2020

(54) METHOD OF USING AN INTRA-ESOPHAGEAL BALLOON SYSTEM

(71) Applicant: Niazi Licensing Corporation, Olympia, WA (US)

(72) Inventor: Imran K. Niazi, Milwaukee, WI (US)

(73) Assignee: Niazi Licensing Corporation, Olympia, WA (US)

(*) Notice: Subject to any disclaimer, the term of this patent is extended or adjusted under 35 U.S.C. 154(b) by 328 days.

(21) Appl. No.: 15/786,707

(22) Filed: Oct. 18, 2017

(65) Prior Publication Data

US 2018/0050181 A1 Feb. 22, 2018

Related U.S. Application Data

(62) Division of application No. 12/847,018, filed on Jul. 30, 2010, now Pat. No. 9,937,329.

(60) Provisional application No. 61/272,564, filed on Oct. 6, 2009.

(51) Int. Cl.
*A61M 25/10* (2013.01)
*A61M 29/02* (2006.01)

(52) U.S. Cl.
CPC .. *A61M 25/1002* (2013.01); *A61M 25/10181* (2013.11); *A61M 29/02* (2013.01); *A61M 25/10185* (2013.11); *A61M 2025/1047* (2013.01); *A61M 2025/1059* (2013.01)

(58) Field of Classification Search
CPC ........ A61B 2018/00488; A61B 5/6853; A61B 2017/00557; A61B 5/037; A61B 5/4233; A61M 29/02; A61M 25/1018; A61M 2025/1059; A61M 2025/1047
See application file for complete search history.

(56) References Cited

U.S. PATENT DOCUMENTS

| 2,077,453 | A | | 3/1934 | Albright | |
|---|---|---|---|---|---|
| 4,955,377 | A | | 9/1990 | Lennox et al. | 607/105 |
| 5,048,532 | A | | 9/1991 | Hickey | 600/488 |
| 5,170,803 | A | * | 12/1992 | Hewson | A61N 1/0517 600/374 |
| 5,531,776 | A | * | 7/1996 | Ward | A61N 1/0517 128/898 |
| 5,662,608 | A | | 9/1997 | Imran | A61M 25/1002 604/103.07 |
| 5,716,386 | A | | 2/1998 | Ward et al. | 607/106 |
| 5,766,151 | A | | 6/1998 | Valley et al. | 604/103.07 |

(Continued)

*Primary Examiner* — Katherine M Shi
*Assistant Examiner* — Michael G Mendoza
(74) *Attorney, Agent, or Firm* — Boyle Fredrickson S.C.

(57) ABSTRACT

A method is disclosed for selective inflation of an inflatable body, such as a balloon, received through an oral cavity and into the esophagus of a patient. The inflatable body is operably coupled to a pressurized fluid source. The inflatable body has a relatively flexible portion and a relatively inflexible portion. When pressurized fluid is delivered to the body to inflate the body, the flexible portion expands more than the inflexible portion, resulting in asymmetrical expansion and movement of the esophagus away from the ablation site to avoid accidental injury while performing a procedure on the patient's left atrium. This movement may be opposite from or directly away from the heart or, alternatively, may be sideways relative to the heart to a location in which the esophagus is interposed between the ablation site and the phrenic nerve.

17 Claims, 4 Drawing Sheets

(56) References Cited

U.S. PATENT DOCUMENTS

| | | | |
|---|---|---|---|
| 6,015,382 A | 1/2000 | Zwart | A61B 17/0218 600/207 |
| 6,067,990 A * | 5/2000 | Kieturakis | A61B 17/0218 128/898 |
| 6,146,339 A | 11/2000 | Biagtan et al. | A61M 25/09 600/585 |
| 6,217,548 B1 | 4/2001 | Tsugita et al. | |
| 7,101,387 B2 | 9/2006 | Garabedian et al. | |
| 7,621,908 B2 | 11/2009 | Miller | |
| 8,454,588 B2 * | 6/2013 | Rieker | A61M 25/0147 606/191 |
| 2003/0144682 A1 | 7/2003 | Qureshi et al. | |
| 2004/0020491 A1 | 2/2004 | Fortuna | |
| 2004/0210281 A1 | 10/2004 | Dzeng et al. | |
| 2006/0118127 A1 | 6/2006 | Chinn | |
| 2007/0055328 A1 | 3/2007 | Mayse et al. | |
| 2007/0066968 A1 | 3/2007 | Rahn | |
| 2007/0118097 A1 | 5/2007 | Miller | |
| 2007/0225701 A1 * | 9/2007 | O'Sullivan | A61B 18/1492 606/41 |
| 2008/0033415 A1 | 2/2008 | Rieker et al. | |
| 2008/0125708 A1 | 5/2008 | Feng | |
| 2008/0161890 A1 | 7/2008 | Lafontaine | |
| 2008/0177175 A1 | 7/2008 | Mottola et al. | 600/424 |
| 2008/0243112 A1 | 10/2008 | De Neve | |
| 2009/0069875 A1 | 3/2009 | Fishel | |

* cited by examiner

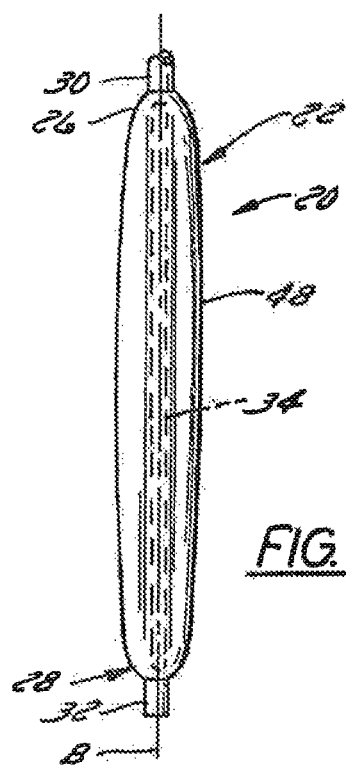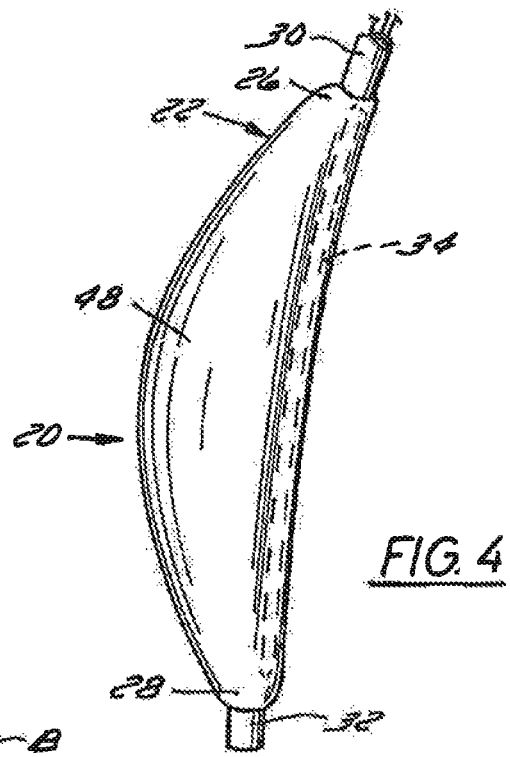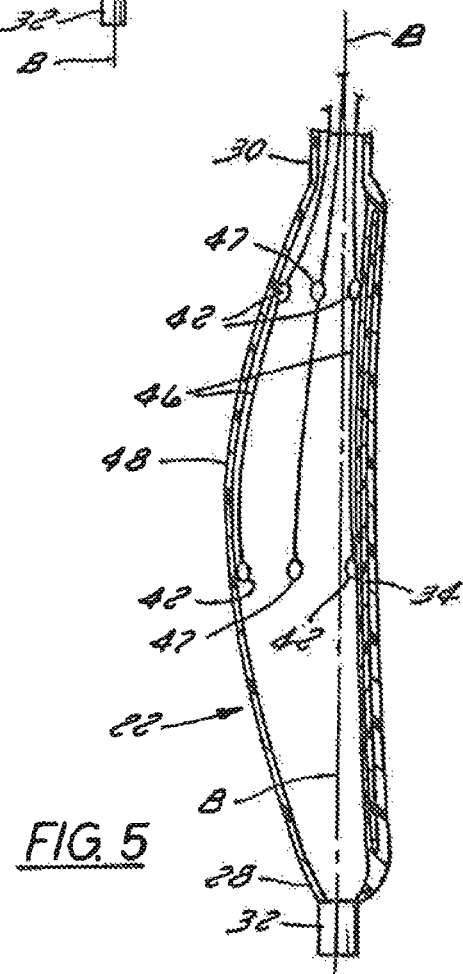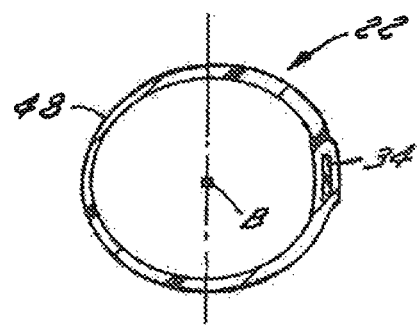

METHOD OF USING AN INTRA-ESOPHAGEAL BALLOON SYSTEM

CROSS REFERENCE TO RELATED APPLICATION(S)

This application is a divisional of U.S. pat. app. Ser. No, 12/847,018, filed Jul. 30, 2010 and entitled INTRA-ESOPHAGEAL BALLOON SYSTEM, which claims priority from U.S. Provisional Patent Application Ser. No. 61/272,564, filed on Oct. 6, 2009, the entire contents of each of which is hereby expressly incorporated by reference into the present application in its entirety.

BACKGROUND OF THE INVENTION

1. Field of the Invention

The invention generally relates to atrial ablation procedures. More particularly, the invention relates to a method of moving a patient's esophagus away from an ablation site to prevent accidental damage to the esophagus during the performance of an ablation.

2. Discussion of the Related Art

Atrial fibrillation is the most common human arrhythmia. The incidence of atrial fibrillation increases with the age of the patient, and thus, the incidence of atrial fibrillation is becoming more prevalent as the average lifespan continue to increase. Atrial fibrillation is associated with increased morbidity and mortality and, in particular, a general decrease in quality of life for those afflicted with atrial fibrillation. Patients are at an increased risk of stroke unless they are treated adequately with anticoagulants. Anticoagulant treatment however, increases a patient's risk of bleeding, which carries with it its own set of dangers. Medications currently available for treating atrial fibrillation have proven to be only moderately effective in decreasing the incidence of recurrent atrial fibrillation, and these mediations do not decrease the patient's risk of having a stroke.

One method of treating atrial fibrillation has been to perform ablation of selected areas of the left atrium. There is evidence to suggest that ablating these areas of the left atrium serves to cure or prevent further incidences of atrial fibrillation, which thereby has shown to reduce the risk of stroke and reduce the necessity of anticoagulant therapy. Typically, ablations of this type are carried out via an intravascular catheter using radiofrequency or microwave energy to cause thermal damage to the selected parts of the left atrial tissue.

The posterior wall of the left atrium is particularly targeted for ablation because the pulmonary veins enter the atrium at this area of the Left atrium. Thus, encircling the pulmonary veins with continuous rings of lesions is common in this procedure. The esophagus may however, be positioned so as to overlie one or more of these veins, thereby making the desired encirclement difficult or impossible. A significant and lethal complication of atrial fibrillation ablation is the accidental creation of an atrio-esophageal fistula following the development of lesions on the posterior wall of the left atrium. Because the esophagus is generally closely positioned to the posterior wall of the left atrium, thermal injury may be communicated to the esophageal wall resulting in disruption of the wall and formation of the atria-esophageal fistula.

In addition to the foregoing, fractionated electrograms and vagal plexi are also frequently present on the posterior wall of the left atrium. These are also common targets of atrial fibrillation ablation. Again, the location of the esophagus may hinder application. of a sufficient energy to successfully ablate enough tissue of the left atrium to prevent recurrence of atrial fibrillation. Further, the esophagus is a mobile structure. Thus, peristaltic movements thereof may cause the esophagus to move and change its position relative to the left atrium. Advanced intracardiac ultrasound systems that are used to locate the esophagus to prevent accidental damage thereto are often incapable of accounting for or tracking such movements, thus rendering these relatively complex and expensive systems ineffective. Fluoroscopic evaluation of the esophagus is also used to determine the position of the esophagus during ablation procedures like this however; such methods provide only two-dimensional information and thus may lead to misreading of the position of the esophagus as it relates to the left atrium.

In addition to the foregoing disadvantages, left atrial ablation of this kind also experiences a great deal of unwanted heat dissipation from the ablation catheter tip. Upon application of the catheter tip to the ablation site, the tissue immediately contiguous to the tip is heated, thereby disrupting cellular function thereof. A sufficient amount of heat must be generated to coagulate and denature the proteins in the myocardial cells. If a heat sink is present in close approximation of the ablation site, generating sufficient heat becomes difficult if not impossible using presently available RF generators. For instance, arteries in close approximation to the ablation site experience rapid blood flow sufficient to conduct heat away from the area rapidly.

Other methods, such as cryoablation and high frequency ultrasound, are still considered experimental and are associated with particular disadvantages specific to these types of ablation.

It has recently been discovered that successful atrial fibrillation ablation may require the introduction of lesions near the location of the inferior right pulmonary vein, which is located in close proximity to the phrenic nerve. Thus, it is has become more common for accidental injury to the phrenic nerve to occur. The phrenic nerve is responsible for operation of the diaphragm, and thus, injury to the phrenic nerve can be quite catastrophic. Thus, a method or system for preventing such injuries is deemed highly desirable.

The need therefore exists to provide a device for carrying out atrial fibrillation ablation of the left atrium that does not suffer from the foregoing disadvantages. In particular, a device for moving the esophagus away from the left atrium of the heart is desired.

SUMMARY OF THE INVENTION

In accordance with a first aspect of the invention, a system for safely performing left atrial fibrillation ablation is provided. In particular, the system according to the invention is configured for selective movement of the esophagus away from the heart and the left atrium thereof such that the necessary areas of the left atrium may be ablated to prevent recurrent atrial fibrillation. By moving the esophagus from the ablation site, the esophagus is maintained at a safe distance from the ablation site and in particular the ablation RF catheter such that the esophagus is not accidentally injured during the performance of the ablation procedure.

The system of the invention includes an inflatable body, most typically a balloon, constructed primarily of a flexible material adapted for insertion into a patient's body through the oral cavity of the patient and into the esophagus. The balloon expands asymmetrically upon inflation to force the esophagus which contains the balloon to also bend and move away from the posterior wall of the atrium. Bending of the esophagus may be directed to also push the phrenic nerve away from the inferior pulmonary vein. The balloon may be inflated by a fluid such as air or another inert gas or, more preferably, by a liquid.

Asymmetrical expansion may be facilitated by forming one strip or portion of the balloon from a material that has a relatively flexible portion and a remainder of the balloon from a relatively inflexible portion when viewed in transverse cross section. For example, a portion adjacent the patient's heart could be made relatively inflexible through the use of a stiffening strip. Because the stiff area of the balloon does not expand as much as the remainder of the balloon, the area of the esophagus adjacent thereto is not contacted by the balloon at this area. Thus, the inflexible portion of the balloon preferably is positioned in the esophagus adjacent the left atrium of the heart such that this portion of the esophagus remains a sufficient distance away from the left atrium such that, upon inflation of the balloon, the balloon is inflated and the esophagus bends away from the area of the left atrium to be ablated The system may include a relief valve for selective expulsion of excess fluid therefrom.

A liquid used to inflate the balloon may be radio-opaque so as not to interfere with imaging of the esophagus and/or heart with X-ray or fluoroscopic examination and/or may be cooled to act as a heat sink during ablation.

In one embodiment of the invention, a number of electrodes are embedded, attached, or otherwise coupled to the wall of the balloon and interconnected by way of a conductor to an electrical power source. The electrodes may communicate with a 3D mapping system such that the location of the esophagus vis-a-vis the electrodes can be determined such that the operator may assess the position of the esophagus while performing the ablation procedures, In addition to or instead of the electrodes, one or more magnetic dipoles may be provided in communication with a magnetically operated 3D mapping system to operate in much the same manner. One or more temperature sensors also may be provided for monitoring the effects of the ablation procedure on the esophagus.

Various other features, embodiments and alternatives of the present invention will be made apparent from the following detailed description taken together with the drawings. It should be understood, however, that the detailed description and specific examples, While indicating preferred embodiments of the invention, are given by way of illustration and not limitation. Many changes and modifications could be made within the scope of the present invention without departing from the spirit thereof, and the invention includes all such modifications.

BRIEF DESCRIPTION OF THE DRAWINGS

In the Drawings:

FIG. 3 is a side elevation view of part of a balloon of the intra-esophageal balloon of the system of FIGS. 1 and 2, showing the balloon in a deflated state;

FIG. 4 is a side el elevation view of the balloon of FIG. 3, showing the balloon in an inflated state;

FIG. 5 is a side sectional elevation view of the balloon in its inflated state of FIG. 4.

FIG. 6 is an end sectional elevation view of the balloon of the invention;

Preferred exemplary embodiments of the invention are illustrated in the accompanying drawings, in which like reference numerals represent like parts throughout, and in which:

DETAILED DESCRIPTION OF THE PREFERRED EMBODIMENTS

Figure 1:
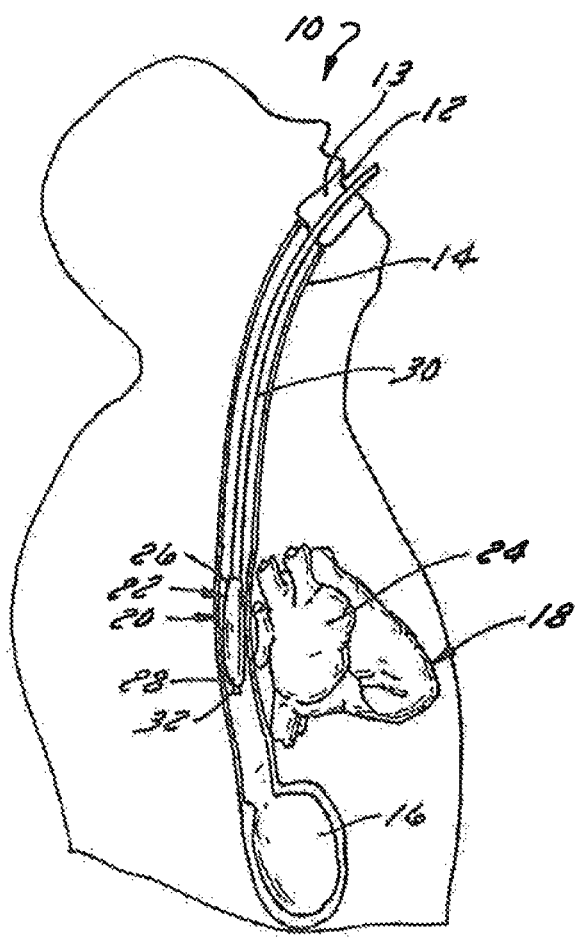
FIG. 1 is a schematic illustration of a patient having an intra-esophageal balloon system constructed in accordance with a preferred embodiment the invention inserted into the patient's esophagus.
Figure 2:
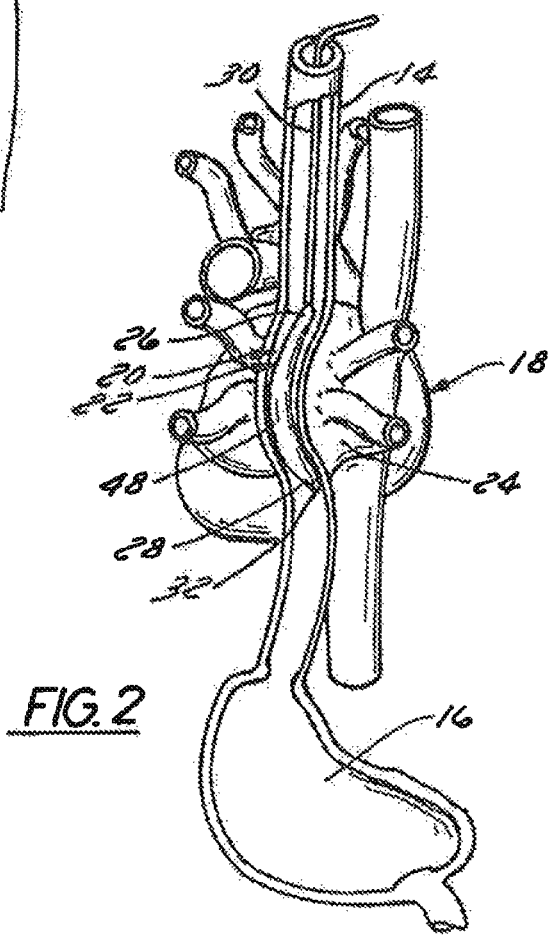
FIG. 2 is a partially cut away isometric view corresponding to FIG. 1.

Referring now to the drawings, and initially FIG. 1, a schematic illustration of a portion of the internal organs of a patient 10 is provided with an intra-esophageal balloon system 20 constructed in accordance with a preferred embodiment of the invention inserted therein. Patient 10 has a mouth 12 leading to the esophagus 14, which then terminates at an opening of the stomach 16. The esophagus 14 is in close proximity to patient's heart 18, placing the esophagus at risk to injury during left atrial ablation.

Figure 7:
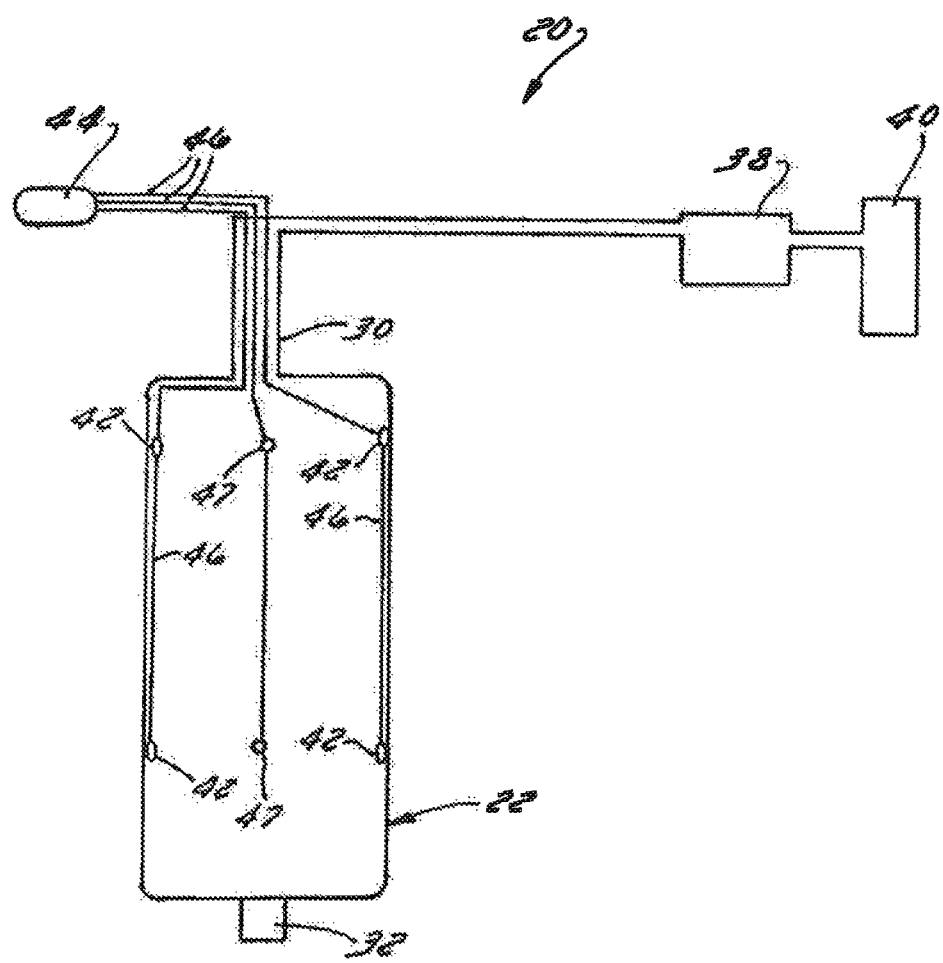
FIG. 7 is a schematic representation of the intra-esophageal balloon system of FIGS. 1 and 2.

The intra-esophageal balloon system 20 is inserted through the patient's mouth 12 and oral cavity 13 and into the esophagus 14. In particular, a balloon 22 of the system 20 is positioned within the esophagus 14 at a point substantially lateral to a left atrium 24 of the heart 18, Balloon 22 comprises a proximal or upper end 26 and a distal or lower end 28 opposite proximal end 26. Proximal end 26 is interconnected with a tube 30 that extends upwardly through the esophagus 14 and through patient's mouth 12 to a source of pressurized liquid, shown at 40 in FIG. 6 and described in detail below. The balloon 22 is designed to expand asymmetrically when inflated by fluid from the source 38, 40 (FIG. 7) to bend, distort, or otherwise move the esophagus 14 away from the heart 18 and facilitate left atrial ablation without thermal injury to the esophagus. When inflated in the absence of an obstruction such as in the open air, the balloon 22 expands at least 5% more, and preferably 15% more on one side of a longitudinal bisector "B" of the balloon 22 than the other side. Balloon 22 may be configured to be inflated to pressures of approximately 8-10 atmospheres. When balloon 22 is inflated, balloon 22 may be 4-7 cm long and less than or equal to 2 cm in diameter, although alternative ranges are envisioned and are within the scope of the present invention. A relief valve 32 is disposed at the distal end 28 of the balloon 22 to prevent its over-inflation. The balloon 22 preferably is inflated with a liquid such as saline, admixed with radiopaque contrast material, although air or another inert gas could be used to inflate balloon 22.

Referring now to FIGS. 3-6, balloon 22 comprises an elongate, relatively narrow balloon constructed of silicone, rubber or a similar flexible material that may be safely introduced into the esophagus, With momentary reference to FIG. 6, balloon 22 is generally circular cross-section when uninflated so as to be symmetrical about a longitudinal bisector B, though it is contemplated that the balloon 22 may be more ovoid or have other shapes, so long as the balloon can be inserted into the patient's esophagus 14 in its deflated state and inflated as discussed below.

Figure 8:
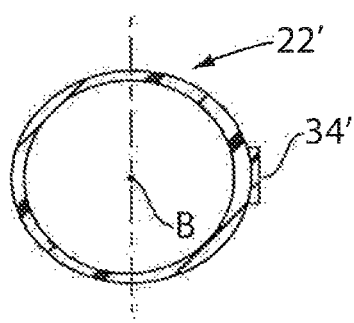
FIG. 8 is an end sectional elevation view of a balloon constructed in accordance with an alternative embodiment of the invention.

As mentioned briefly above, balloon 22 is configured to expand asymmetrically when inflated so as to distort the esophagus 14 away from the heart 18. Asymmetrical expansion may be made possible by rendering the balloon circumferentially non-uniformly flexible. This effect is most easily achieved by making at least one side or edge portion of the balloon more or less flexible than at least one other side or edge portion of the balloon. In the illustrated embodiment, this capability is enabled by providing a longitudinally-extending stiffening strip 34 along a side portion thereof. Stiffening strip 34 is constructed of a material that is substantially more rigid than the remainder of the material of which balloon 22 is constructed, such as a relatively hard plastic material. Stiffening strip 34 is mounted on, in, or integrally formed with the remainder of the balloon 22. Stiffening strip 34 preferably is applied along one relatively peripheral narrow portion of balloon 22 at a location at or near the portion of the esophagus 14 that is closest to the patient's heart 18 and extends lengthwise from proximal end 26 to distal end 28 without extending distally beyond the distal end. Stiffening strip 34 preferably has a width similar to that of an average width of a patient's esophagus for reasons that will be made apparent from the ensuing description. In particular, stiffening strip 34 may have a width of approximately 1 mm to 2 cm. In particular, as can be best seen in FIG. 4, stiffening strip 34 is configured to inhibit or prevent a portion of balloon 22 from expanding during inflation of balloon 22. Stiffening strip 34 may be a wire or piece of fishing line embedded into or attached to a wall of balloon 22. Stiffening strip 34 is shown as being embedded in the wall of balloon 22 in FIGS. 1-6. In an alternative embodiment, shown in FIG. 8, the stiffening strip 34' is mounted to an exterior of the balloon 22'. In both embodiments, the entire inner circumference of the balloon is constructed from a flexible material. In one embodiment, stiffening strip 34 has a radiopaque marker affixed to it to identify the location of the stiffening strip 34 when using imaging equipment. In this manner, balloon 22 may be oriented under fluoroscopy or other imaging techniques to ensure proper positioning of stiffening strip 34 with respect to the esophagus 14.

As will be explained in detail, balloon 22 is configured to be inflated by way of a fluid or preferably a liquid that is introduced through tube 30. Because the tube 30 has an outlet terminating at an inlet of the balloon 22 as seen in FIG. 5, no structures extend completely through the balloon between the proximal and distal ends thereof, as can be clearly seen in. FIG. 5. In addition, since the distal end of the tube 20 terminates at the proximal end of the balloon 22, stiffening strip 34 extends beneath the distal end of the tube 20, again as clearly illustrated in FIG. 5. As the liquid is introduced into balloon 22, balloon 22 begins to inflate and expand around the portions constructed from the flexible material. On the other hand, the portion of balloon 22 incorporating the stiffening strip 34 will expand less than the remainder of the balloon, if at all. The resultant inflation of balloon 22 in a non-uniform or asymmetrical manner causes the balloon 22 to bend or bow relative to the longitudinal bisector B of the uninflated result. As a result of this, the balloon distorts from the uninflated state shown in FIGS. 1 and 3 in which the balloon 22 extends linearly as a whole and is symmetrical about the longitudinal bisector B. When the balloon 22 is in the inflated state shown in FIGS. 2 and 4, the balloon as a whole extends significantly non-linearly so that the curvature of the balloon as whole, including the stiffening strip 34, is substantially increased in a common direction relative to the longitudinal bisector B of the uninflated balloon 22. The resulting high curvature is especially evident in FIG. 2, in which the balloon 22 is shown as having a generally crescent shape when viewed in profile. The bending of the balloon 22 as a whole moves the esophagus 14 away from the patient's heart as can been in FIG. 2. The bending increases progressively from the ends of the balloon towards its center such that esophageal distortion is maximized at or near the ablation site.

Other mechanisms could be used instead of or in addition to the stiffening strip to cause asymmetrical inflation. For example, the stiffness of a strip of the balloon extending along the side of the balloon opposite the heart could be reduced, e.g., by reducing its thickness. This "reduced stiffness strip" could be provided instead of or in addition to a stiffening strip at the opposite side of the balloon near the heart. Either strip could have varying stiffening or weakening properties at different locations along its length so as to tailor the location of maximum asymmetrical distortion to a desired portion of the balloon 22. Either strip could be continuous and extend at least generally the entire length of the balloon as illustrated, or could extend along only along part of the length of the balloon 22, as a continuous strip or in discrete aligned or misaligned segments. Alternatively, strips of reduced and/or enhanced stiffness could be provided along portion(s) of the balloon that are between the side adjacent the heart and the side opposite the heart, causing the balloon to bend sideways away from the ablation site.

Relief valve 32 is configured to prevent over-inflation of balloon 22 and resultant possible injury to esophagus 14 by preventing the fluid pressure in the balloon from exceeding a certain predetermined level. Relief valve 32 can be any kind of relief valve generally known in the art that simply opens at the threshold pressure to release the excess liquid into the esophagus 14 and the stomach 16 and that automatically closes when the pressure in the balloon 22 drops below the predetermined pressure. The predetermined pressure preferably is settable using suitable controls located on or in the valve 32.

Referring now to FIGS. 1-7, opposite the relief valve 32, balloon 22 is coupled to tube 30 at the proximal end 26 thereof. Tube 30 extends upwardly from balloon 22 through the oral cavity and out of mouth 12. An inner lumen of balloon 22 is continuous with the lumen of tube 30 to thereby prevent leaking of fluid from tube 30. Tube 30 preferably is constructed from a relatively flexible medical grade material that is compatible with insertion into a patient and is generally cylindrical in shape. The opposite end of tube 30 is connected to a liquid delivery device, such as a pump 38, shown schematically in FIG. 7. Tube 30 and pump 38 may be coupled by way of a stopcock, valve, or similar such interconnection permitting the selected supply of pressurized fluid to the balloon 22. A pressure reducer and/or pressure regulator may be provided within the pump 38 or between the pump 38 and the balloon 22 to supplement or even replace the relief valve 32.

Pump 38 may be a mechanical or electrical pump. Pump 38 is connected to a reservoir 40 holding a quantity of fluid for delivery to balloon 22. Preferably, the fluid held in reservoir 40 is cooled to promote esophageal cooling during ablation. In particular, reservoir 40 may hold iced saline or a similar such biocompatible fluid. In a preferred embodiment, the fluid held in reservoir 40 is a radiopaque coolant fluid. As stated briefly above, by using a relatively cool fluid to inflate balloon 22, the tube 30 and balloon 22 serve to provide a so-called heat-sink to further reduce the risk of perforating or otherwise damaging the esophagus during ablation of the heart 18.

The coolant also preferably is radiopaque, such as having been treated with a radiopaque dye of the kind known in the art. In this manner, the esophagus 14 is readily visible using X-rays or other imaging techniques while the fluid is flowing through the tube 30 while tube 30 is inserted into the esophagus 14. Accordingly, the operator carrying out the procedure is able to view the esophagus 14 during inflation of balloon 22 such that he or she may better observe the location of the esophagus 14 with respect to the heart 18 and, in particular, the left atrium 24 of the heart. Thus, the operator is able to determine whether esophagus 14 has been moved sufficiently far from the heart 18 such that he or she may safely perform an ablation thereon. A radio-opaque fluid also permits the ablation process to be imaged without obstruction from the balloon 22.

With particular reference to FIG. 5, one embodiment of the invention is shown in which a number of electrodes 42 are inserted into the balloon 22 via tube 30. In particular, electrodes 42 are disposed within the wall of balloon 22. Electrodes 42 are coupled to a power source 44 (see FIG. 7) by way of an electrical conductor 46, which extends upwardly through tube 30 and out of the tube 30 for interconnection with power source 44. Power source 44 may be an electrical connection assembly of the kind known in the art configured to supply a predetermined amount of electricity to the electrodes 42. The electrodes 42 by way of conductor 46 may be interfaced with a three-dimensional electro-anatomical mapping system of the kind generally known in the art. In this manner, balloon 22 is capable of being viewed by the operator at a display screen in three-dimensions. Thus, balloon 22 may be viewed in relation to the ablation site on heart 18 at any given time. Alternatively, electrodes 42 may be replaced by magnetic dipoles that allow the location of the balloon 22 to be detected using a magnetically-based three-dimensional mapping system such as CARTO 3D or a similar known system.

Alternatively, or in addition to, electrodes 42, balloon 22 may include a number of temperature sensors 47 incorporated into the balloon 22 cavity or wall. The temperature sensors may be interconnected with a temperature monitoring assembly such that the operator may be able to monitor a temperature of the balloon 22 during ablation of left atrium 24 of heart 18. In one embodiment of the invention, if the temperature exceeds a predetermined value, the system 20 of the invention may be configured to automatically respond. For example, system 20 may be configured to respond to prevent a lesion from forming or expanding by flooding the balloon 22 with additional fluid When a particular predetermined temperature is detected. The system 20 may be interfaced with the power source of the ablation mechanism such that the ablation itself is also terminated.

In operation, balloon 22 is introduced into the esophagus 14 through the oral cavity 13 via the mouth 12 to a location in which it is substantially adjacent to, and preferably parallel with, the left atrium 24 of heart 18, It is positioned such that the stiffening strip 34 is located adjacent a portion of the esophagus that is relatively close to the heart. Accordingly, when balloon 22 is inflated asymmetrically but circumferentially, the adjacent portion of the esophagus 14 will be moved away from the heart 18. More specifically, the operator actuates pump 38 and/or related controls to supply pressurized fluid into the tube 30 and thence into balloon 22. As balloon 22 begins to inflate with the introduction of the fluid thereto, the balloon 22 expands asymmetrically in the direction of the flexible portion 48 thereof As can be seen from a review of FIG. 4, the expansion of the flexible portion 48 of balloon 22 causes the balloon 22 to bow or bend in the direction of the expansion, eventually contacting the sidewall of the esophagus adjacent thereto. As the flexible portion 48 continues to expand, it begins to exert a force on the esophagus 14 such that esophagus 14 moves in a direction of the applied force or away from the heart 18. In this manner, as can best be seen from FIG. 2, the esophagus becomes bowed at or about the region adjacent heart 18 to move directly away from or sideways relative to the left atrium such that the caregiver is free to begin the ablation of left atrium 24 of heart 18. If the balloon 22 is configured and oriented such that, when the balloon is inflated, the esophagus 14 moves sideways away from the ablation site to interpose itself between the phrenic nerve and the left atrial lesion, the esophagus 14 can provide a barrier or protection against accidental damage to the phrenic nerve. At its maximum point of distortion, the esophagus preferably moves at least 5 mm, and more preferably at least 20 mm, laterally away from its initial position.

When the fluid used to inflate the balloon is a coolant, the coolant in the balloon 22 also serves as a heat sink sufficient to mitigate or even prevent injury to the phrenic nerve, or balloon 22 may assist in mobilizing the nerve such that it is positioned out of the way of the ablation site.

After the ablation procedure is complete, the balloon 22 is deflated by operation of the relief valve 32 or otherwise and removed from the esophagus.

Although the best mode contemplated by the inventors of carrying out the present invention is disclosed above, practice of the present invention is not limited thereto. It will be manifest that various additions, modifications and rearrangements of the aspects and features of the present invention may be made in addition to those described above without deviating from the spirit and scope of the underlying inventive concept. The scope of some of these changes is discussed above. The scope of other changes to the described embodiments that fall within the present invention but that are not specifically discussed above will become apparent from the appended claims and other attachments.

I claim:

1. A method of moving a human esophagus comprising the steps of:
   inserting an uninflated selectively inflatable balloon into a patient's esophagus, wherein, when viewed in transverse cross section, the balloon has a relatively flexible portion and a relatively inflexible portion, both extending longitudinally of the balloon; and
   inflating the balloon asymmetrically sufficiently to cause the balloon as a whole to bow or bend so as to move at least a portion of the esophagus transversely away from an initial position thereof.

2. The method of claim 1, wherein, when the balloon is inserted into the esophagus, the relatively inflexible portion of the balloon is positioned closer to the patient's heart than the relatively flexible portion, and wherein the at least a portion of the esophagus moves away from the patient's heart as a result of balloon inflation, and further comprising, while the balloon is in the inflated state thereof;
   ablating tissue of the patient's heart; then
   deflating the balloon; and then
   removing the balloon from the esophagus.

3. The method of claim 1, wherein the step of inflating the balloon is accomplished. by pumping a pressurized liquid into the balloon.

4. The method of claim 3, further comprising the step of cooling the liquid, wherein the cooled liquid serves to provide the esophagus with a heat sink such that the esophagus is further protected against injury during the ablating step.

5. The method of claim 3, further comprising the step of releasing excess pressure from the balloon by opening a relief valve located at a distal end of the balloon.

6. The method of claim 1, wherein, at a maximum point of distortion thereof, the esophagus moves at least 5 mm laterally away from its initial position as a result of balloon inflation.

7. The method of claim 6, wherein, at the maximum point of distortion thereof, the esophagus moves at least 20 mm laterally away from its initial position as a result of balloon inflation.

8. The method of claim 1, wherein
the balloon has a proximal end and a distal end, wherein
in an uninflated state thereof, the balloon extends at least generally linearly and has a longitudinal bisector extending from the proximal end thereof to the distal end thereof, and wherein
upon inflation of the balloon, the balloon expands asymmetrically and circumferentially about the longitudinal bisector of the balloon while bowing or bonding such that the balloon as a whole, including the relatively inflexible portion, is bent or bowed in a common direction relative to the longitudinal bisector so as to take on a crescent shape when viewed in profile.

9. The method of claim 1, wherein, when inflated, the balloon is 4-7 cm long.

10. The method of claim 1 wherein, when inflated, the balloon has a maximum diameter of less than 2 cm.

11. The method of claim 1, further comprising, using information received from electrodes positioned within the balloon and communicated to a 3D mapping system, determining a location of the esophagus while performing an ablation procedure.

12. The method of claim 1, wherein the balloon has a proximal end and a distal end, and wherein the relatively inflexible portion of the tube is formed by a stiffening strip that that extends longitudinally between the proximal and distal ends of the balloon without protruding distally beyond the distal end of the balloon.

13. The method of claim 1, wherein the stiffening strip has a width of less than 2 mm.

14. A method comprising:
providing a selectively inflatable balloon which has a proximal end and a distal end and which, when viewed in transverse cross section, has a relatively inflexible portion and a relatively flexible portion both extending longitudinally of the balloon, the inflexible portion of the balloon being formed by a stiffening strip that extends longitudinally between the proximal and distal ends of the balloon without protruding distally beyond the distal end of the balloon, wherein, in an uninflated state thereof, the balloon extends at least generally linearly and has a longitudinal bisector extending from the proximal end thereof to the distal end thereof,
inserting the balloon in a human patient's esophagus such the relatively inflexible portion of the balloon is positioned nearer the patient's heart than the relatively flexible portion; then
inflating the balloon such that the balloon expands and assumes an inflated state in which the balloon is expanded asymmetrically but circumferentially about an axial centerline of the balloon and asymmetrically about the longitudinal bisector of the balloon and in which the balloon as a whole, including the relatively inflexible portion, is bent or bowed in a common direction relative to the longitudinal bisector;
while the balloon is inflated and the portion of the esophagus is moved away from the patient's heart, performing an ablation procedure on the patient's heart; then
deflating the balloon; and then
removing the balloon from the patient's esophagus.

15. The method as recited in claim 14, wherein the inflating step comprises pumping a cooled liquid into the balloon at a temperature lower than the patient's body temperature, the liquid serving as a heat sink during the ablation procedure.

16. The method as recited in claim 13, wherein, during the inflating step, the balloon interposes itself between the patient's phrenic nerve and the patient's left atrium.

17. The method as recited in claim 14, wherein, upon achieving the inflated state thereof, the balloon moves a portion of the esophagus at least 5 mm furtheraway from the patient's heart.

* * * * *